(12) United States Patent
Jarisch

(10) Patent No.: US 11,123,032 B2
(45) Date of Patent: Sep. 21, 2021

(54) WIDE AREA SINGLE OR DUAL GUIDED BREAST TISSUE TOMOGRAPHY AND TOMOSYNTHESIS IMAGING SYSTEMS AND METHODS

(71) Applicant: Wolfram R. Jarisch, Potomac, MD (US)

(72) Inventor: Wolfram R. Jarisch, Potomac, MD (US)

(*) Notice: Subject to any disclaimer, the term of this patent is extended or adjusted under 35 U.S.C. 154(b) by 0 days.

(21) Appl. No.: 16/210,994

(22) Filed: Dec. 5, 2018

(65) Prior Publication Data

US 2019/0239840 A1  Aug. 8, 2019

Related U.S. Application Data

(60) Provisional application No. 62/594,994, filed on Dec. 5, 2017.

(51) Int. Cl.
*A61B 17/32* (2006.01)
*A61B 6/00* (2006.01)
(Continued)

(52) U.S. Cl.
CPC ............ *A61B 6/502* (2013.01); *A61B 5/4312* (2013.01); *A61B 6/0435* (2013.01);
(Continued)

(58) Field of Classification Search
None
See application file for complete search history.

(56) References Cited

U.S. PATENT DOCUMENTS 5,308,321 A  5/1994  Castro
6,304,770 B1  10/2001  Lee et al.
(Continued)

FOREIGN PATENT DOCUMENTS

DE  102005048049 B4  9/2010

OTHER PUBLICATIONS

Jamalian et al., Demonstration and Analysis of the Suction Effect for Pumping Lymph from Tissue Beds at Subatmospheric Pressure, Nature, Sci. Rep. 2017; 7: 12080.
(Continued)

*Primary Examiner* — Hoon K Song
(74) *Attorney, Agent, or Firm* — Baker Botts L.L.P.; Michael A. Sartori

(57) ABSTRACT

A breast imaging system comprises: a wide area tissue receptacle adapted to be coupled to an imaging apparatus, the imaging apparatus having an imaging volume, the wide area tissue receptacle defining a wide area tissue volume, the wide area tissue volume at least partially intersecting the imaging volume to form a wide area tissue imaging volume, the wide area tissue receptacle having an opening that is sufficiently wide to accept an entire breast into the wide area tissue receptacle, the wide area tissue receptacle having a sealing interface below the opening adapted to create a seal between tissue and the wide area tissue receptacle; and a pump coupled to the wide area tissue receptacle, the pump adapted to apply negative pressure to the wide area tissue volume to form the seal between the sealing interface and the tissue, and the pump further adapted to apply negative pressure to pull the breast into the wide area tissue volume, a diagnostic volume being defined as a portion of the breast intersecting the wide area tissue imaging volume.

24 Claims, 7 Drawing Sheets

(51) Int. Cl.
*A61B 8/08* (2006.01)
*A61B 6/04* (2006.01)
*A61B 5/00* (2006.01)
*A61B 6/02* (2006.01)

(52) U.S. Cl.
CPC .......... *A61B 6/4429* (2013.01); *A61B 8/0825* (2013.01); *A61B 6/025* (2013.01); *A61B 6/04* (2013.01)

(56) References Cited

U.S. PATENT DOCUMENTS

| | | |
|---|---|---|
| 7,742,796 B2 | 6/2010 | Eberhard et al. |
| 8,792,965 B2 | 7/2014 | Ning et al. |
| 9,808,214 B2 | 11/2017 | Smith et al. |
| 2002/0004630 A1 | 1/2002 | Sarvazyan et al. |
| 2003/0233110 A1* | 12/2003 | Jesseph ................ A61B 6/0414 606/167 |
| 2004/0073106 A1 | 4/2004 | Lee et al. |
| 2004/0081273 A1 | 4/2004 | Ning |
| 2004/0082856 A1 | 4/2004 | Marmarelis |
| 2009/0171244 A1 | 7/2009 | Ning et al. |
| 2009/0213986 A1 | 8/2009 | Thaler |
| 2010/0177866 A1 | 7/2010 | Shibuya |
| 2012/0114096 A1 | 5/2012 | Lebovic et al. |
| 2015/0282715 A1 | 10/2015 | Lemke |

OTHER PUBLICATIONS

International Search Report & Written Opinion issued in International Patent Application No. PCT/US18/64123 dated Feb. 15, 2019.

* cited by examiner

WIDE AREA SINGLE OR DUAL GUIDED BREAST TISSUE TOMOGRAPHY AND TOMOSYNTHESIS IMAGING SYSTEMS AND METHODS

CROSS-REFERENCE TO RELATED APPLICATIONS

This patent application claims the benefit of U.S. Patent Application No. 62/594,994, filed on Dec. 5, 2017, and the entire contents are hereby incorporated by reference.

FIELD OF INVENTION

The invention relates to the field of breast tissue tomography and tomosynthesis imaging.

SUMMARY

A breast imaging system according to some embodiments of the invention comprises: a wide area tissue receptacle adapted to be coupled to an imaging apparatus, the imaging apparatus having an imaging volume, the wide area tissue receptacle defining a wide area tissue volume, the wide area tissue volume at least partially intersecting the imaging volume to form a wide area tissue imaging volume, the wide area tissue receptacle having an opening that is sufficiently wide to accept an entire breast into the wide area tissue receptacle, the wide area tissue receptacle having a sealing interface below the opening adapted to create a seal between tissue and the wide area tissue receptacle; and a pump coupled to the wide area tissue receptacle, the pump adapted to apply negative pressure to the wide area tissue volume to form the seal between the sealing interface and the tissue, and the pump further adapted to apply negative pressure to pull the breast into the wide area tissue volume, a diagnostic volume being defined as a portion of the breast intersecting the wide area tissue imaging volume.

A method for imaging a soft tissue according to some embodiments of the invention comprises: introducing the breast into a wide area tissue volume, the wide area tissue volume at least partially intersecting an imaging volume of an imaging apparatus to form a wide area tissue imaging volume; creating a seal with tissue at a perimeter of the wide area tissue volume; applying negative pressure to the wide area tissue volume to pull the breast into the wide area tissue volume, a diagnostic volume being defined as a portion of the breast intersecting the wide area tissue imaging volume; and imaging the diagnostic volume.

BRIEF DESCRIPTION OF THE DRAWINGS

Exemplary embodiments will now be described in connection with the associated drawings.

DETAILED DESCRIPTION OF THE EMBODIMENTS

Exemplary embodiments of the invention are discussed in detail below. In describing exemplary embodiments, specific terminology is employed for the sake of clarity. However, the invention is not intended to be limited to the specific terminology so selected. A person skilled in the relevant art will recognize that other equivalent components may be employed and other methods developed without departing from the broad concepts of the invention. All references cited herein are incorporated by reference as if each had been individually incorporated.

For tomography, tomosynthesis, and other imaging technologies, scanning the breast or other tissue of interest, diagnostic image quality may be improved by pulling into or retaining tissue deeper in an imaging volume by wide area suction. The suction is applied to:

1. pull a wide area of the tissue surrounding the immediate region of interest, for example near the chest, deeper into the well-imaged scanning area improving the available diagnostic volume; and
2. stretch and elongate the tissue, for example breast tissue, in order to reduce tissue penetrating radiation levels, using, for example, softer and fewer x-rays; and
3. reduce the diameter of the diagnostic relevant tissue volume, less restrained by surrounding tissue, by stretching thereby improving accuracy of image reconstruction; and
4. pull the tissue into suitable, possibly lubricated second form, to obtain locally desired tissue shaping and compression; and
5. facilitate the flow into and possibly accumulation of contrast agent in the reduced internal pressure tissue, especially for one or more regions of interest.

This arrangement allows:

1. to reduce diagnostic beam hardness; and
2. to reduce total x-ray dose deposition in the diagnostic relevant tissue volume, for example the breast, using less and softer radiation; and
3. to reduce scatter in the reduced tissue cross-section; and
4. to record sharper images due to reduced, for example, x-ray focal spot size and movement artifact associated with shorter exposure times; and
5. to bring, especially dense breast tissue with higher disease risk factors and often tighter imaging constraints, deeper into the imaging area; and
6. to provide faster and better controllable flow of contrast agent into the soft tissue; and
7. to pull tissue, for example, close to the hard underlying structures, into the imaging area; and 8. provide greater patient comfort, for example, by minimizing tension and compression of breast tissue, by, for example, wider distribution of possibly smaller forces in the tissue.

Figure 1A:
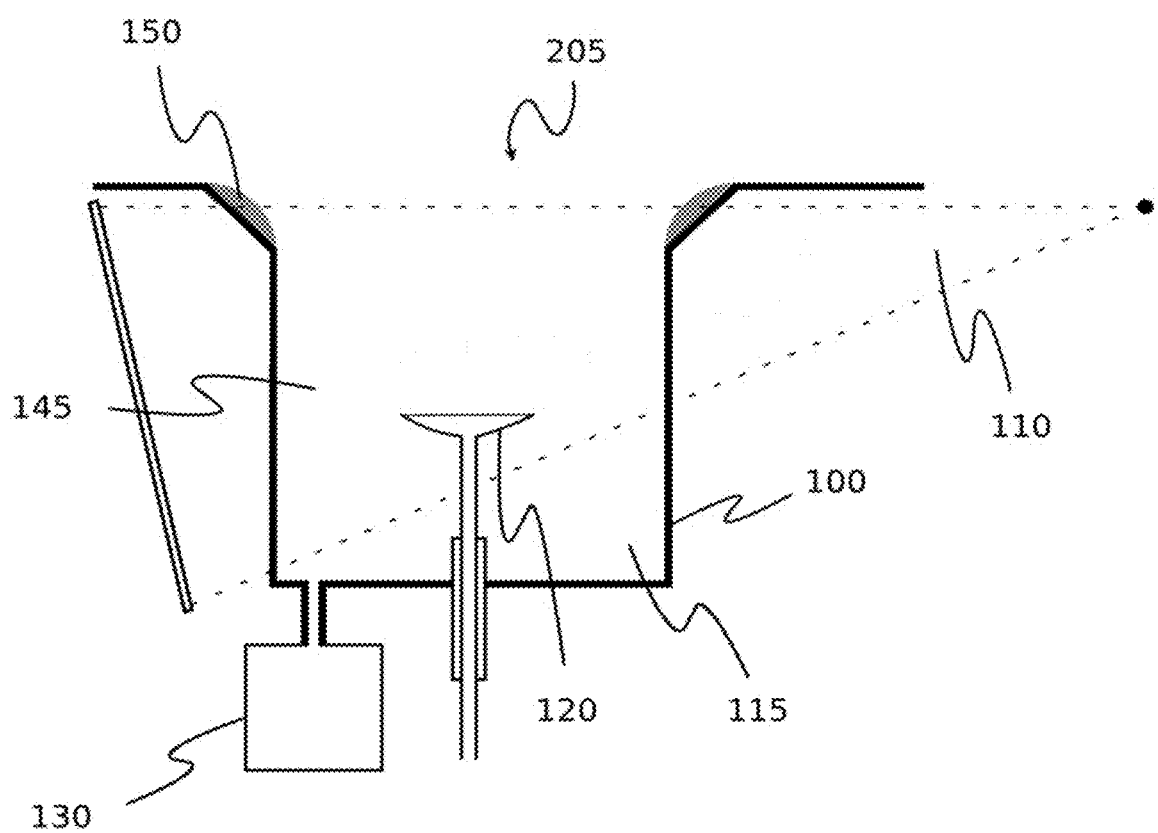
FIG. 1A shows a side view of an example of the wide area guided breast imager (WAGBI) according to some embodiments of the invention.
Figure 1B:
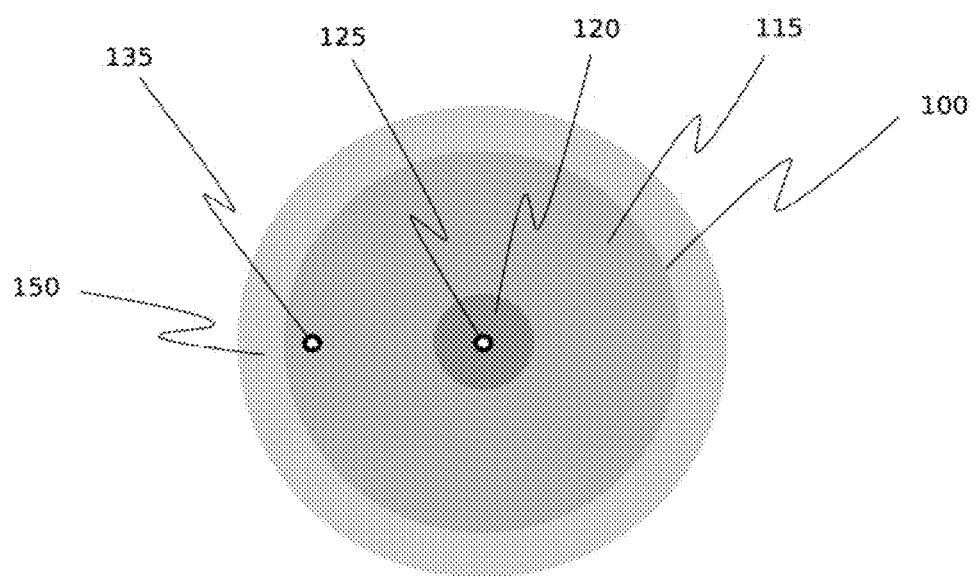
FIG. 1B shows a top view of an example of the breast entry area of the WAGBI according to some embodiments of the invention.

FIGS. 1A and 1B depict an example of the wide area guided breast imager (WAGBI) according to some embodiments. The breast imaging system according to some embodiments comprises a wide area tissue receptacle 100 adapted to be coupled to an imaging apparatus, the imaging apparatus having an imaging volume 110. The wide area tissue receptacle 100 defines a wide area tissue volume 115. The wide area tissue volume 115 at least partially intersects the imaging volume 110 to form a wide area tissue imaging volume 145.

Figure 1C:
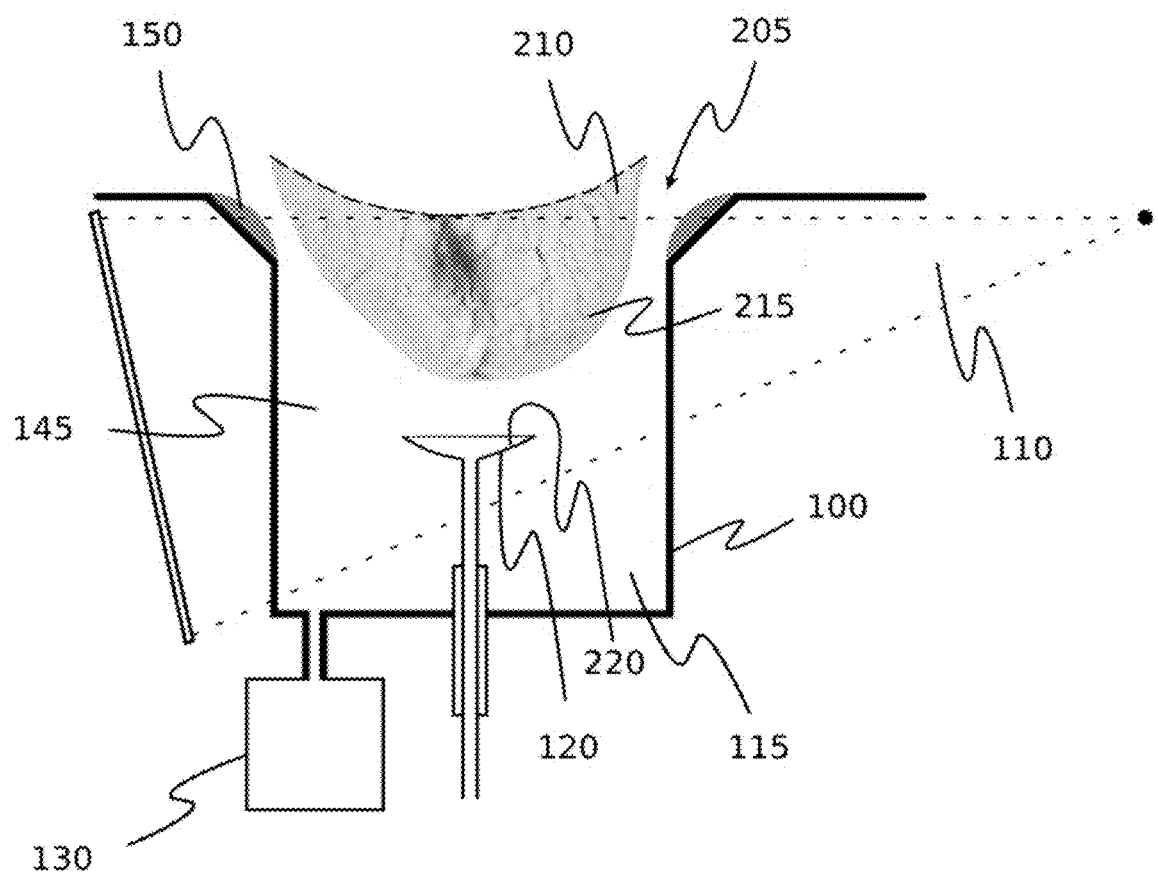
FIG. 1C shows a side view of an example of the WAGBI according to some additional embodiments of the invention.

As shown in FIG. 1C, the wide area tissue receptacle 100 has an opening 205 that is sufficiently wide to accept an entire breast 210 into the wide area tissue receptacle 100. The wide area tissue receptacle 100 has a sealing interface 150 below the opening 205 adapted to create a seal between tissue and the wide area tissue receptacle 100. The sealing interface 150 of the wide area tissue receptacle 100 may include a soft cushion to interface and create a seal with the patient's skin.

The breast imaging system according to some embodiments further comprises a pump 130 coupled to the wide area tissue receptacle 100. The pump 130 is adapted to apply negative pressure to the wide area tissue volume 115 to form the seal between the sealing interface 150 and the tissue. The pump 130 is further adapted to apply negative pressure to pull the breast 210 into the wide area tissue volume 115, a diagnostic volume 215 being defined as a portion of the breast 210 intersecting the wide area tissue imaging volume 145.

According to some embodiments of the invention, the breast imaging system further comprises a secondary tissue receptacle 120 coupled to the wide area tissue receptacle 100. The secondary tissue receptacle 120 can have an inner surface 220 for contacting the breast 210. The secondary tissue receptacle 120 can define a secondary volume within the wide area tissue volume 115. However, the embodiments of the invention are not limited to embodiments including the secondary tissue receptacle 120. The breast imaging system may include a wide area tissue receptacle without a secondary tissue receptacle 120. Further, the position of the secondary tissue receptacle 120 shown in FIG. 1A is provided as an example, but the secondary tissue receptacle 120 can have a different position with respect to the wide area tissue receptacle 100, for example, to facilitate imaging of a particular portion of the breast 210, or imaging from a particular angle. For example, the secondary tissue receptacle 120 can be adaptable to move away from the opening 205 once the breast 220 has been secured to the secondary tissue receptacle 120 to elongate the breast 210.

Figure 2:
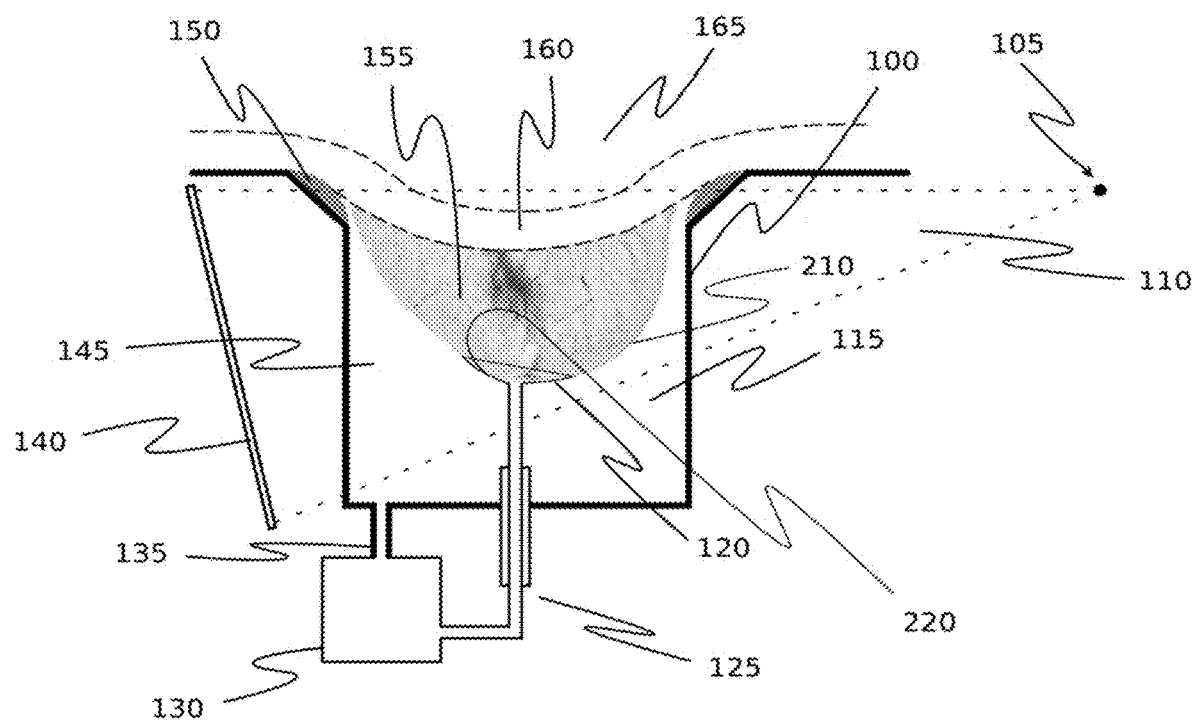
FIG. 2 shows a side view of an example of the WAGBI according to some additional embodiments of the invention.

According to some embodiments, the pump 130 is further adaptable to apply negative pressure to the secondary volume to bring the breast 210 into contact with the inner surface 220 of the secondary tissue receptacle 120, as shown in FIG. 2.

Figure 3:
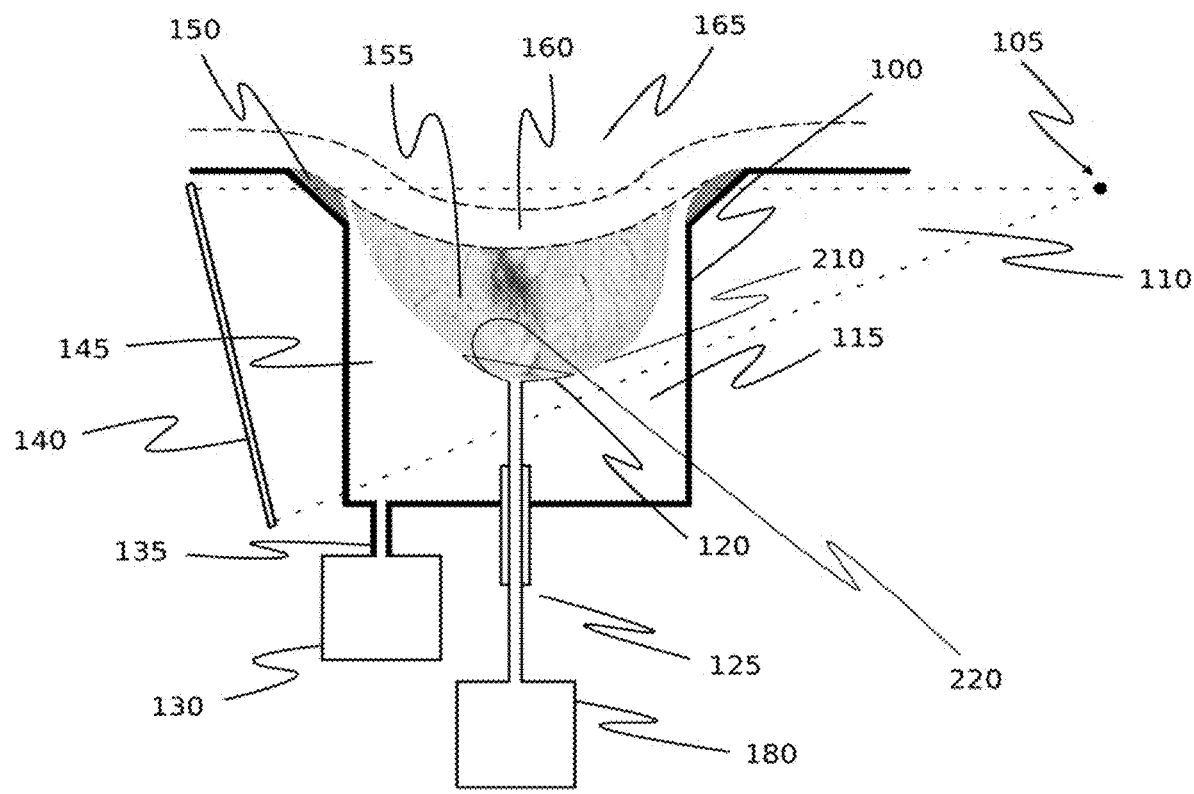
FIG. 3 shows a side view of an example of the WAGBI having two pumps according to some embodiments of the invention.

According to some embodiments, the breast imaging system further comprises a second pump 180, as shown in FIG. 3. According to some embodiments, the second pump can be adaptable to apply negative pressure to the secondary volume to bring the breast 210 into contact with the inner surface 220 of the secondary tissue receptacle 120, as shown in FIG. 3.

According to some embodiments, the secondary tissue receptacle 120 can be adaptable to conform to a shape of the breast 210. In other embodiments, the secondary tissue receptacle 120 can define a shape for the adaptable breast 210 to conform to.

According to some embodiments, the wide area tissue receptacle 100 comprises a first material, and the secondary tissue receptacle 120 comprises a second material. The first material may be the same as the second material, or the first material may be different from the second material. For example, the first and second materials may be non-pliable or non-deformable materials, or the first material may be non-pliable and the second material may be pliable or deformable. The wide area tissue receptacle 100 may generally be stiff to counter the forces created by the negative pressure, but may also include a pliable material at the sealing interface 150 for contacting the patient's tissue.

According to some embodiments, the wide area tissue receptacle 100 can be adapted to be removably coupled to the imaging apparatus, the imaging apparatus having the imaging volume 110. For example, the wide area tissue receptacle may be mechanically coupled to the imaging apparatus such that the wide area tissue receptacle can be secured to and also removed from the imaging apparatus. The secondary tissue receptacle 120 can be disposed in the wide area tissue volume 115. According to some embodiments, the secondary tissue receptacle 120 can be disposed in the secondary tissue receptacle 120 at a position that minimizes intersection with the imaging volume 110.

Figure 4:
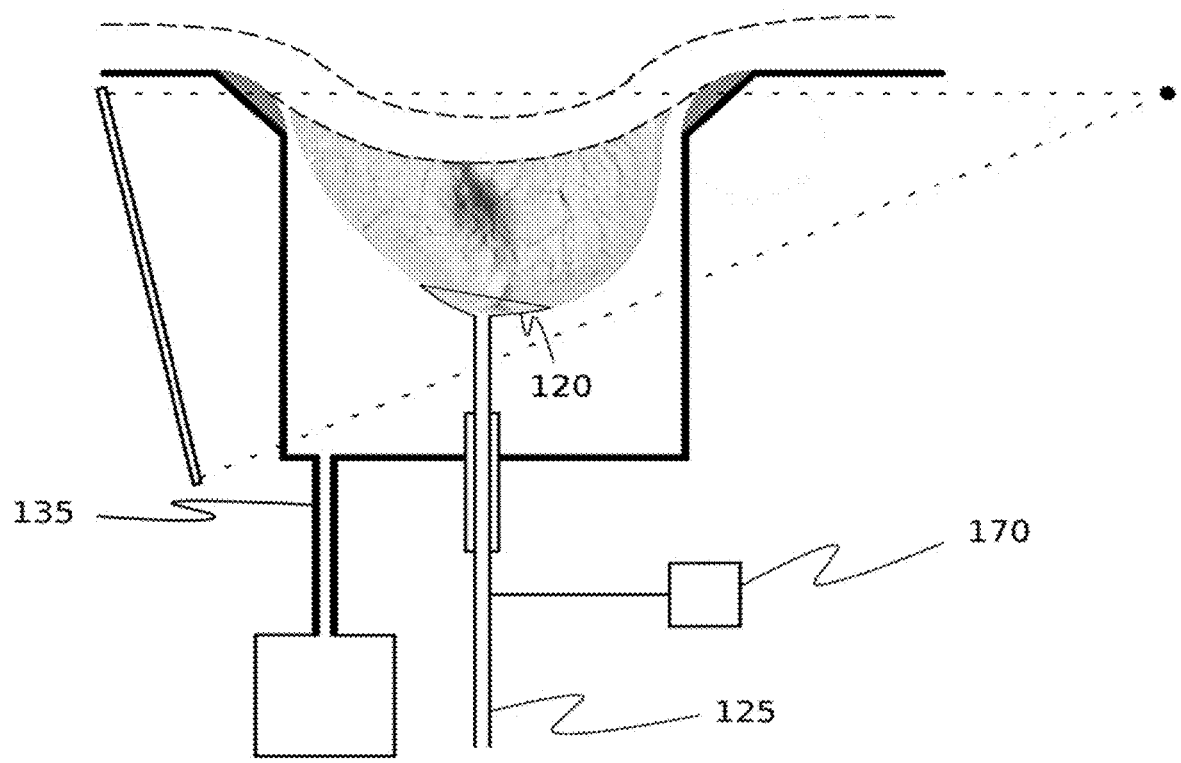
FIG. 4 shows a side view of an example of the WAGBI having one or more sensors coupled to the secondary tissue receptacle according to some embodiments of the invention.

According to some embodiments, the breast imaging system further comprises one or more sensors 170 coupled to the secondary tissue receptacle 120, as shown in FIG. 4. The one or more sensors 170 may be coupled to the secondary tissue receptacle 120 via a coupling tube 125, and may measure a variety of characteristics. For example, the one or more sensors 170 may measure a physical deformation of the secondary tissue receptacle 120. The one or more sensors 170 may measure a physiological characteristic of tissue placed in the secondary tissue receptacle 120. The one or more sensors 170 may measure forces on the secondary tissue receptacle 120. The one or more sensors 170 may measure suction forces in the secondary tissue receptacle 120. The one or more sensors 170 may perform a combination of measurements.

Figure 5:
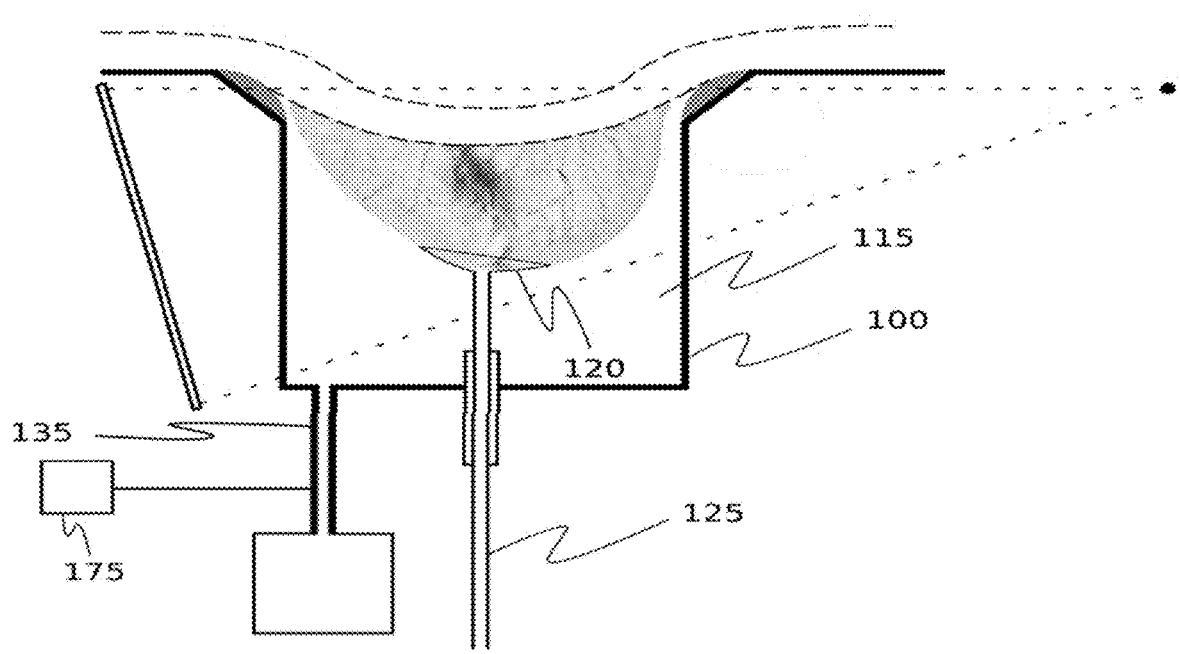
FIG. 5 shows a side view of an example of the WAGBI having one or more sensors coupled to the imaging volume according to some embodiments of the invention.

According to some embodiments, the breast imaging system further comprises one or more sensors 175 coupled to the wide area tissue receptacle 100. As shown in FIG. 5, the one or more sensors 175 may be coupled to the wide area tissue receptacle 100 via the connection path 135. Alternatively or additionally, the one or more sensors 175 may be disposed inside the imaging volume in a way that avoids interference with the imaging process. The one or more sensors 170 and one or more sensors 175 can be very small, for example, on the order of a few $mm^3$. According to some embodiments, the one or more sensors 175 may be one or more pressure sensors coupled to the wide area tissue receptacle 100. According to some embodiments, the one or more sensors 175 may measure the volume of the entire breast tissue 155 pulled into the wide area tissue imaging volume 145.

As depicted in FIGS. 1A and 1B, the wide area tissue receptacle 100 is shown as being cylindrical shaped and having certain locations for the secondary tissue receptacle 120, the coupling tube 125, and the connection path 135. However, the shape of the wide area tissue receptacle 100 and the location of these components are not limited to this example and may be any shape and/or location that is conducive to receiving a tissue for imaging and/or interfacing with the imaging apparatus.

According to some embodiments, the breast imaging system is usable with an imaging system employing Tomosynthesis; X-ray Computed Tomography; Positron Emission Tomography (PET); Single Photon Emission Computed Tomography (SPECT); Magnetic Resonance Imaging (MM); or Ultrasound (US) Imaging.

A method for imaging a soft tissue according to some embodiments comprises introducing a tissue area surrounding a diagnostic volume of a patient's tissue into a wide area tissue volume; creating a seal with the patient's tissue at a perimeter of the wide area tissue volume; applying negative pressure to the wide area tissue volume to pull the diagnostic volume of the patient's tissue into an imaging volume; and imaging the diagnostic volume.

According to some embodiments, the method further comprises, prior to or during imaging the diagnostic volume, applying a force to the diagnostic volume of the patient's tissue to change a shape of the diagnostic volume of the patient's tissue.

Referring again to FIG. 1D, the wide area tissue receptacle 100 defines a wide area tissue volume 115. The secondary tissue receptacle 120 may be disposed in the wide area tissue volume 115, and may be used to pull, shape, or position the breast. A coupling tube 125 can provide mechanical access to the breast, as well as secondary suction access. The coupling tube 125 can be connected to the pump 130 or the second pump 180, as shown in FIGS. 2 and 3, respectively. The wide area tissue receptacle 100 may have a connection path 135 connecting the pump 130 to the wide area tissue volume. The breast imaging system may include an x-ray imaging screen 140 or one or several flat or curved imaging sensors for PET or SPECT. The imaging screen 140 may curve around and even encircle the wide area tissue receptacle 100.

Figure 1D:
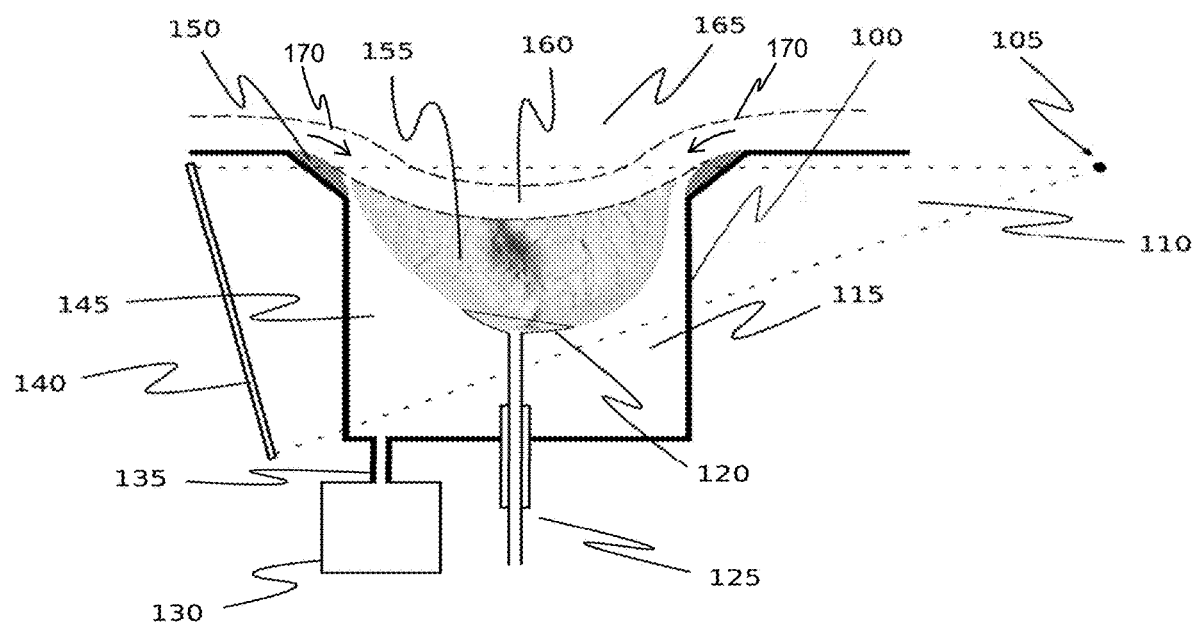
FIG. 1D shows a side view of an example of the WAGBI in one operational mode according to some additional embodiments of the invention.

As shown in FIG. 1D, the patient's entire breast tissue 155 can be positioned inside the imaging volume 110 using the invention. The negative pressure applied to the wide area tissue volume 115 pulls (in the direction of arrows 170) the entire breast tissue 155, the fat tissue 160, and the connective and breast muscle tissue 165 toward the imaging volume 110. The system increases the volume of the patient's tissue that can be imaged by the imaging apparatus, allowing tissues closer to and potentially including the breast muscle tissue 165 to be imaged. The system also prevents excessive pressure from being concentrated on a single area of the patient's tissue.

According to some embodiments, the imaging apparatus has a source 105 having an imaging cone, the imaging cone defining the imaging volume 110 (as indicated by the dotted lines in the figures). For example, the source 105 may be a movable x-ray source having a cone beam emanating from the x-ray source. However, the embodiments of the invention are not limited to x-ray sources. For example, the imaging apparatus may include, but is not limited to, a magnetic resonance imaging apparatus or an ultrasound imaging apparatus. Further, the breast imaging system may include the imaging apparatus. For example, the invention according to some embodiments includes an imaging apparatus and the breast imaging system coupled to the imaging apparatus. Existing imaging systems may also be modified to include the breast imaging system described herein.

An X-ray gantry system, for example, can be located in front of the patient or under a patient table and can rotate the imaging apparatus or measure around the static wide area tissue receptacle 100 and secondary tissue receptacle 120 attached to the patient's tissue. Suction pressure may be provided, for example, from open access 135 through the bottom of the gantry.

Figure 6:
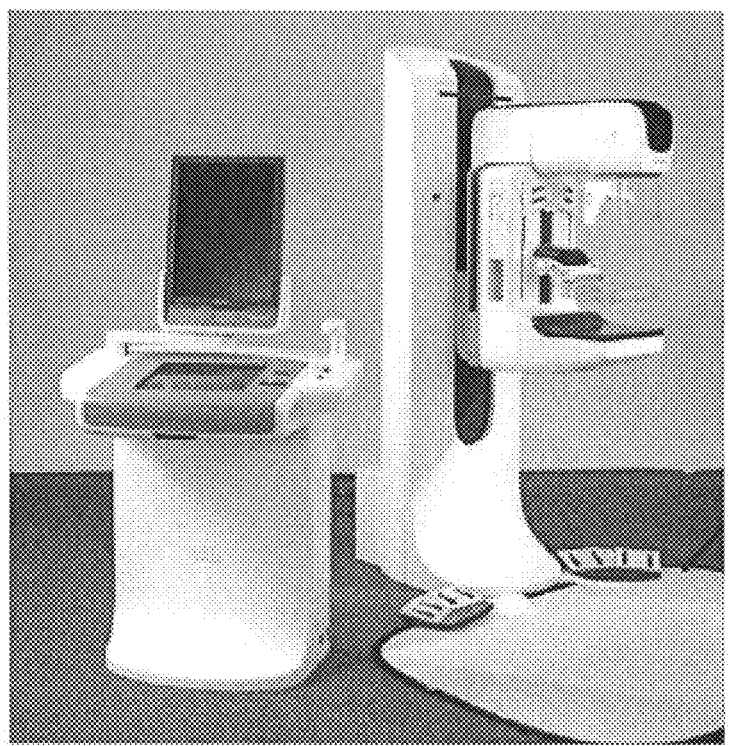
FIG. 6 shows a conventional Hologic tomosynthesis system that requires breast compression, but without tissue suction or tissue pulling.
Figure 7:
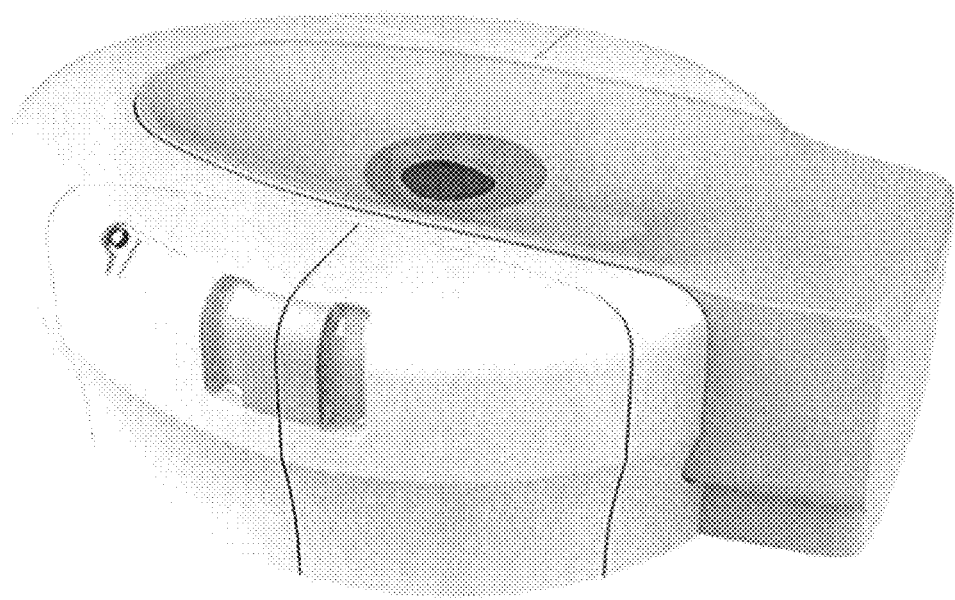
FIG. 7 shows a conventional cone beam computed tomography (CBCT) system (without control console), but without tissue suction or tissue pulling.

FIGS. 6 and 7 depict conventional systems that do not employ suction. FIG. 6 shows a conventional Hologic tomosynthesis system that requires breast compression. FIG. 7 shows a conventional cone beam computed tomography (CBCT) system.

The system of FIGS. 6 and 7 can be modified to implement the above-described WAGBI approach to soft tissue tomosynthesis and tomographic imaging. The patient can be positioned with his or her soft tissue placed between the compression plates of the Hologic tomosynthesis system, or on top of the opening on the CT scanner. The modified imaging system then applies gentle suction of the patient's tissue into the imaging space, and the surrounding tissue forms a seal. For example, the tissue can be supported by an additional soft seal sealing interface at the rim at or below the opening of the imaging space. The suctioned seal may be enhanced by using a gel or lubricant between the tissue and the soft seal. For example, the gel or lubricant may be applied to the rim at the opening of the imaging space and/or to the tissue being imaged. The tissue being suctioned may face downward towards the earth, to use gravity to assist the suctioning. The imaging space may be provided, for example, by a tomosynthesis system, CT reconstruction system, MRI system, sound wave device, or other imaging modality.

More elaborate approaches to achieve suction are, however, possible. The shape of the tissue, for example the breast, influences diagnostic image quality. Suction against a secondary tissue receptacle, also referred to herein as a "preform," located inside the WAGBI, may be used for tissue shaping. The static preform may or may not seal against the remainder of the imaging device, provided a seal at the device opening is effective. For example, using the invention, a conventional 3D CBCT system may be adapted to pull a wide area of tissue surrounding the diagnostic volume deeper into the imaging device by a combination of suction against a seal at the opening of the device and pulling on a preform inside the device, forming a WAGBI. Furthermore, two or more separate suction systems may support positioning. For example, the first suction system may pull tissue sufficiently deep into the imaging device opening, and the second suction device system may keep the tissue suitably matched to the preform. In order to provide best diagnostic efficacy, wide area and secondary preform interfaces can be changed to maintain patient comfort.

Forces and suction pressure delivered by the suction devices should satisfy safety requirements and try to avoid pain and minimize discomfort. Magnitude of tissue pulling forces may, for example, be adjustable in the range of greater than zero to less than or equal to approximately 2 N (ca. 7 oz) per $cm^2$. With the embodiments of the invention any values in this range can be used for tissue pulling forces. Suction differential pressure to the surrounding air pressure may, for example, be adjustable in the range of greater than zero to less than or equal 0.14 bar (ca. 100 mm Hg, or 100 Ton). With the embodiments of the intervention, any values in this range can be used for the suction differential pressure. Strong pulling forces and suction differential pressure may, for example, benefit the imaging of dense, often small, breasts near the underlying chest tissue, and breast tissue in men.

Care should be taken, however, when using high differential suction pressures, for example, more than 0.02 bar (ca. 15 mm Hg, or 0.3 psi), and pulling forces exceeding 0.2

N/cm² of tissue cross-section, to avoid risk of injury to the patient. Furthermore, prolonged suction with differential pressures exceeding a few milli-bar (mbar) (for example, 2.0, 3.0, or 4.0 mbar) (approximately 1.0 mbar corresponds to approximately 0.7 mm Hg) may overcome the negative interstitial tissue pressure of the immobilized tissue and lead to swelling. Similarly, prolonged pulling may cause swelling by locally overcoming interstitial pressures.

Mechanically, a wide variety of designs are possible to provide the above-described functions of suction and pulling. Suction may, for example, be provided by an adjustable low-pressure pump with multiple adjustable outlets that may be controlled by the attending imaging technician. Suction differential pressures, tissue column changes (measurement of imaging volume), and forces may, for example, be recorded with sensors and/or transducers to quantify the intervention and asses risks.

In the discussion above, reference is made to breast tissue. However, the system can be modified to receive other body parts, including but not limited to soft tissues, human or non-human.

The examples and embodiments described herein are non-limiting examples.

The invention is described in detail with respect to exemplary embodiments, and it will now be apparent from the foregoing to those skilled in the art that changes and modifications may be made without departing from the invention in its broader aspects, and the invention, therefore, as defined in the claims is intended to cover all such changes and modifications as fall within the true spirit of the invention.

What is claimed is:

1. A breast imaging system comprising:
   a wide area tissue receptacle adapted to be coupled to an imaging apparatus, the imaging apparatus having an imaging volume,
      the wide area tissue receptacle defining a wide area tissue volume, the wide area tissue volume at least partially intersecting the imaging volume to form a wide area tissue imaging volume,
      the wide area tissue receptacle having an opening that is sufficiently wide to accept an entire breast into the wide area tissue receptacle,
      the wide area tissue receptacle having a sealing interface below the opening adapted to create a seal between tissue and the wide area tissue receptacle;
   a pump coupled to the wide area tissue receptacle,
      the pump adapted to apply negative pressure to the wide area tissue volume to form the seal between the sealing interface and the tissue, and
      the pump further adapted to apply negative pressure to pull the breast into the wide area tissue volume, a diagnostic volume being defined as a portion of the breast intersecting the wide area tissue imaging volume; and
   a secondary tissue receptacle coupled to the wide area tissue receptacle, the secondary tissue receptacle having an inner surface for contacting the breast, the secondary tissue receptacle defining a secondary volume within the wide area tissue volume,
      wherein the secondary tissue receptacle is adaptable to conform to a shape of the breast, and
      wherein the wide area tissue receptacle is closed at an end opposite the opening to enclose all portions of the breast that are accepted into the opening upon creation of the seal between the tissue and the wide area tissue receptacle without exposing any portion of the breast outside of the wide area tissue receptacle.

2. The breast imaging system of claim 1, wherein the pump is further adaptable to apply negative pressure to the secondary volume to bring the breast into contact with the inner surface of the secondary tissue receptacle.

3. The breast imaging system of claim 1, further comprising a second pump, wherein the second pump is adaptable to apply negative pressure to the secondary volume to bring the breast into contact with the inner surface of the secondary tissue receptacle.

4. The breast imaging system of claim 1, wherein the wide area tissue receptacle comprises a first material, and wherein the secondary tissue receptacle comprises a second material that is different from the first material.

5. The breast imaging system of claim 1, wherein the secondary tissue receptacle is disposed in the imaging volume.

6. The breast imaging system of claim 1, further comprising a sensor to measure a physical deformation of the secondary tissue receptacle.

7. The breast imaging system of claim 1, further comprising a sensor to measure a physiological characteristic of tissue placed in the secondary tissue receptacle.

8. The breast imaging system of claim 1, wherein the secondary tissue receptacle is made of a material with known effects on imaging radiation signal changes.

9. The breast imaging system of claim 1, further comprising a sensor coupled to the secondary tissue receptacle to measure forces on the secondary tissue receptacle.

10. The breast imaging system of claim 1, wherein the secondary tissue receptacle is adaptable to pull, position, or shape the breast.

11. The breast imaging system of claim 1, wherein the wide area tissue receptacle is adapted to be removably coupled to the imaging apparatus, the imaging apparatus having the imaging volume.

12. The breast imaging system of claim 1, further comprising a pressure sensor coupled to the wide area tissue receptacle.

13. The breast imaging system of claim 1, further comprising two or more pressure sensors coupled to the wide area tissue receptacle.

14. The breast imaging system of claim 1, further comprising a sensor within the imaging volume to measure the diagnostic volume of the tissue pulled into the wide area tissue imaging volume.

15. The breast imaging system of claim 1, wherein the breast imaging system is usable with an imaging system employing
   Tomosynthesis;
   X-ray Computed Tomography;
   Positron Emission Tomography;
   Single Photon Emission Tomography;
   Magnetic Resonance Imaging; or
   Ultrasound Imaging.

16. A system comprising:
   the imaging apparatus, and
   the breast imaging system of claim 1 coupled to the imaging apparatus and within the imaging field of the imaging apparatus.

17. A method for imaging a breast comprising:
   introducing the breast through an opening of a wide area tissue receptacle into a wide area tissue volume defined by the wide area tissue receptacle, the wide area tissue volume at least partially intersecting an imaging volume of an imaging apparatus to form a wide area tissue imaging volume;

creating a seal with tissue at a perimeter of the wide area tissue volume;

applying negative pressure to the wide area tissue volume to pull the breast into the wide area tissue volume, a diagnostic volume being defined as a portion of the breast intersecting the wide area tissue imaging volume;

applying negative pressure to a secondary tissue receptacle within the wide area tissue volume, the secondary tissue receptacle having an inner surface for contacting the breast, the secondary tissue receptacle defining a secondary volume within the wide area tissue volume; and imaging the diagnostic volume, wherein the secondary tissue receptacle is adaptable to conform to a shape of the breast, wherein the wide area tissue receptacle is closed at an end opposite the opening to enclose all portions of the breast that are accepted into the opening upon creation of the seal between the tissue and the wide area tissue receptacle without exposing any portion of the breast outside of the wide area tissue receptacle.

18. The method for imaging a breast according to claim 17, further comprising:

prior to or during imaging the diagnostic volume, applying a force to the breast to change a shape of the diagnostic volume.

19. The breast imaging system of claim 1, wherein the wide area tissue receptacle comprises a non-pliable first material, and wherein the secondary tissue receptacle comprises a pliable or deformable second material.

20. The breast imaging system of claim 1, wherein the opening of the wide area tissue receptacle is sufficiently wide to accept the entire breast, fat tissue, and connective and breast muscle tissue into the wide area tissue receptacle, wherein the pump further is adapted to apply negative pressure to pull the entire breast, the fat tissue, and the connective and breast muscle tissue into the wide area tissue volume, and wherein the diagnostic volume includes the portion of the breast, a portion of the fat tissue, and a portion of the connective and breast muscle tissue intersecting the wide area tissue imaging volume.

21. The method for imaging a breast according to claim 17, wherein the negative pressure applied to the wide area tissue volume pulls the breast in entirety, fat tissue, and connective and breast muscle tissue into the wide area tissue volume, and wherein the diagnostic volume includes the portion of the entire breast, a portion of the fat tissue, and a portion of the connective and breast muscle tissue intersecting the wide area tissue imaging volume.

22. A breast imaging system comprising:

a wide area tissue receptacle adapted to be coupled to an imaging apparatus, the imaging apparatus having an imaging volume, the wide area tissue receptacle defining a wide area tissue volume, the wide area tissue volume at least partially intersecting the imaging volume to form a wide area tissue imaging volume, the wide area tissue receptacle having an opening that is sufficiently wide to accept an entire breast into the wide area tissue receptacle, the wide area tissue receptacle having a sealing interface below the opening adapted to create a seal between tissue and the wide area tissue receptacle;

a pump coupled to the wide area tissue receptacle, the pump adapted to apply negative pressure to the wide area tissue volume to form the seal between the sealing interface and the tissue, and the pump further adapted to apply negative pressure to pull the breast into the wide area tissue volume, a diagnostic volume being defined as a portion of the breast intersecting the wide area tissue imaging volume; and a secondary tissue receptacle coupled to the wide area tissue receptacle, the secondary tissue receptacle having an inner surface for contacting the breast, the secondary tissue receptacle defining a secondary volume within the wide area tissue volume, wherein the secondary tissue receptacle defines a shape for the breast to conform to, and wherein the wide area tissue receptacle is closed at an end opposite the opening to enclose all portions of the breast that are accepted into the opening upon creation of the seal between the tissue and the wide area tissue receptacle without exposing any portion of the breast outside of the wide area tissue receptacle.

23. The method for imaging a breast according to claim 17, wherein the negative pressure applied to the secondary tissue receptacle has a magnitude greater than or equal to the negative pressure applied to the wide area tissue volume.

24. The breast imaging system of claim 1, wherein the secondary volume defined by the second tissue receptacle is configured to enclose and fully cover an end of the breast without exposing any part of the end of the breast.

* * * * *